United States Patent
Song et al.

(10) Patent No.: US 9,084,838 B2
(45) Date of Patent: Jul. 21, 2015

(54) FEMININE CARE ABSORBENT ARTICLE FOR USE IN WARM CLIMATES

(75) Inventors: Xuedong Song, Roswell, GA (US); FuLiang Cheng, Taoyuan (TW)

(73) Assignee: Kimberly-Clark Worldwide, Inc., Neenah, WI (US)

(*) Notice: Subject to any disclaimer, the term of this patent is extended or adjusted under 35 U.S.C. 154(b) by 252 days.

(21) Appl. No.: 13/021,094

(22) Filed: Feb. 4, 2011

(65) Prior Publication Data
US 2012/0203190 A1  Aug. 9, 2012

(51) Int. Cl.
A61F 13/20 (2006.01)
A61L 15/56 (2006.01)
A61L 15/46 (2006.01)

(52) U.S. Cl.
CPC ............ A61L 15/56 (2013.01); A61L 15/46 (2013.01); A61L 2300/21 (2013.01); A61L 2300/404 (2013.01)

(58) Field of Classification Search
None
See application file for complete search history.

(56) References Cited

U.S. PATENT DOCUMENTS

| | | | |
|---|---|---|---|
| 4,163,039 A | | 7/1979 | Emrich |
| 4,287,153 A | * | 9/1981 | Towsend ..................... 422/412 |
| 4,798,603 A | | 1/1989 | Meyer et al. |
| 4,801,494 A | | 1/1989 | Datta et al. |
| 4,908,026 A | | 3/1990 | Sukiennik et al. |
| 5,183,742 A | * | 2/1993 | Omoto et al. .................. 435/14 |
| 5,217,445 A | * | 6/1993 | Young et al. .................. 604/381 |
| 5,248,309 A | | 9/1993 | Serbiak et al. |
| 5,843,055 A | * | 12/1998 | Seger ............................ 604/365 |
| 6,472,358 B1 | * | 10/2002 | Richter et al. ................. 510/234 |
| 6,542,379 B1 | | 4/2003 | Lauffer et al. |
| 6,603,403 B2 | * | 8/2003 | Jeutter et al. .................. 340/604 |
| 6,772,708 B2 | * | 8/2004 | Klofta et al. .................. 116/206 |
| 6,904,865 B2 | | 6/2005 | Klofta |
| 7,159,532 B2 | * | 1/2007 | Klofta et al. .................. 116/206 |
| 7,241,627 B2 | * | 7/2007 | Wilhelm et al. .............. 436/518 |
| 7,265,257 B2 | * | 9/2007 | Baldwin et al. ............... 604/364 |
| 7,883,997 B2 | | 2/2011 | Yoshida |
| 7,947,467 B2 | | 5/2011 | Kritzman et al. |
| 2007/0134307 A1 | | 6/2007 | Xiao et al. |
| 2008/0300558 A1 | | 12/2008 | Brusk et al. |

(Continued)

FOREIGN PATENT DOCUMENTS

CN 101562970 A 10/2009

OTHER PUBLICATIONS

Machine Translation of Japanese Patent No. 2000-279442, Oct. 10, 2000, 9 pages.

(Continued)

*Primary Examiner* — Tan-Uyen (Jackie) T Ho
*Assistant Examiner* — Eric Bryant
(74) *Attorney, Agent, or Firm* — Dority & Manning, P.A.

(57) ABSTRACT

A feminine care absorbent article (e.g., feminine care pad, sanitary napkin, tampon, etc.) is provided that employs a synergistic combination of an antimicrobial composition for inhibiting the growth of microorganisms (e.g., bacteria, protozoa, yeast, fungi, etc.) and a pH sensor for signaling to the user when the antimicrobial composition is no longer operating at its full capacity. In this manner, the user can initially wear the article without fear of infection. After a certain period of time, the user can visually inspect the color of the pH sensor to obtain an indication of whether the antimicrobial composition is still active and effective in inhibiting microorganism growth, or whether it is time to replace or remove the article.

21 Claims, 1 Drawing Sheet

(56) References Cited

U.S. PATENT DOCUMENTS

| | | |
|---|---|---|
| 2009/0157024 A1 | 6/2009 | Song |
| 2009/0157025 A1 | 6/2009 | Song et al. |
| 2009/0275908 A1* | 11/2009 | Song .............. 604/361 |
| 2010/0030173 A1 | 2/2010 | Song et al. |
| 2010/0047303 A1 | 2/2010 | Yhlen et al. |
| 2010/0114047 A1 | 5/2010 | Song et al. |
| 2010/0262100 A1 | 10/2010 | Klofta |
| 2011/0015063 A1 | 1/2011 | Gil et al. |
| 2011/0015597 A1 | 1/2011 | Gil et al. |
| 2011/0015598 A1 | 1/2011 | Song et al. |
| 2011/0015599 A1 | 1/2011 | Song et al. |
| 2011/0144603 A1 | 6/2011 | Song |
| 2011/0152816 A1 | 6/2011 | Zhou et al. |

OTHER PUBLICATIONS

Morris et al., "Bio-sensing textile based patch with integrated optical detection system for sweat monitoring," *Sensors and Actuators B: Chemical*, vol. 139, No. 1, Nov. 18, 2009, pp. 231-236.

Schlatter, Sarah, "Bio-sensing textile based patch for sweat monitoring," Biomedical Engineer, University of Rhode Island.

Cost, Frank, "Pocket Guide to Digital Printing," Delmar Publishers, Albany, NY, ISBN 0-8273-7592-1, pp. 144-145.

ASTM E 1164-02 entitled "Standard Practice for Obtaining Spectrometric Data for Object-Color Evaluation," Current Edition Approved Jun. 10, 2002, Published Aug. 2002, 8 pages.

Colorimetry (CIE No. 15.2), 1986, 87 pages.

ISO 7724/1—Paints and varnishes—Colorimetry—Part 1: Principles, Oct. 1, 1984, 8 pages.

JIS (Japanese Industrial Standard) Z 8722:2000, Methods of colour measurement—Reflecting and transmitting objects, Date of Establishment—Feb. 27, 1959, Date of Revision—May 20, 2000, 63 pages.

Search Report and Written Opinion for PCT/IB2012/050143 dated Aug. 22, 2012, 13 pages.

\* cited by examiner

FEMININE CARE ABSORBENT ARTICLE FOR USE IN WARM CLIMATES

BACKGROUND OF THE INVENTION

The female vagina is naturally colonized by a variety of bacteria, yeast, and microorganisms. For example, a normal vagina generally contains more than about $10^4$ lactobacilli per milliliter of vaginal material. Under normal conditions, the vagina flora provides a mildly acidic environment that helps guard against the invasion of pathogenic microbes (e.g., *Gardnerella vaginalis, Candida albicans*, etc.). Unfortunately, this vaginal balance may be easily upset by a variety of external factors that ultimately lead to vaginal infection. One such external factor may be the climate. For example, in tropical climates, the consistently warm conditions can lead to a high degree of sweating near the vaginal region. An increase in moisture content due to sweating may stimulate the growth of pathogenic microorganisms, which may potentially lead to infection. This problem may be particularly acute during a female's menstrual cycle when pads or other feminine care articles are used. More particularly, in addition to absorbing menstrual fluids, the feminine care articles may also retain moisture secreted by the user due to sweating. The presence of this additional moisture could eventually offset the activity of any antimicrobial agents employed in the feminine care article. This fear may lead to a lack in confidence by users that the antimicrobial agents will function in the desired manner.

As such, a need currently exists for a feminine care absorbent article that is well suited for warm climates, and that can help inhibit the growth of pathogenic microorganisms and also provide a signal to the user that such an antimicrobial system is beginning to lose or has lost its efficacy.

SUMMARY OF THE INVENTION

In accordance with one embodiment of the present invention, a feminine care absorbent article is disclosed that comprises a generally liquid-impermeable layer, a liquid-permeable layer, an absorbent core positioned between the generally liquid-impermeable layer and the liquid-permeable layer. The article also comprises an antimicrobial composition that is disposed on the liquid-permeable layer and a sensor that comprises a pH-sensitive composition. The antimicrobial composition comprises an acidic compound. Further, the sensor is integrated into the article and positioned such that the pH-sensitive composition is in fluid communication with a bodily fluid from a user of the article. The pH-sensitive composition includes a chromogen that undergoes a visible color change upon contact with the bodily fluid, the visible color change occurring at a pH level of from about 3 to about 9.

In accordance with another embodiment of the present invention, a method for determining when to remove a feminine care absorbent article from a wearer is disclosed. The feminine care absorbent article comprises an antimicrobial composition and a sensor, wherein the antimicrobial composition comprises an acidic compound and the sensor comprises a pH-sensitive composition. The pH-sensitive composition includes a chromogen that undergoes a visible color change within a pH range of from about 3 to about 9 so that the pH-sensitive composition exhibits a first color at pH values of less than about 3 and a second color at pH values of about 9 or more. The method comprises visually observing the sensor to determine whether the pH-sensitive composition has the second color, which is indicative of a need to remove the feminine care absorbent article.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGURE in which.

Repeat use of references characters in the present specification and drawing is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a feminine care absorbent article (e.g., feminine care pad, sanitary napkin, tampon, etc.) that employs a synergistic combination of an antimicrobial composition for inhibiting the growth of microorganisms (e.g., bacteria, protozoa, yeast, fungi, etc.) and a pH sensor for signaling to the user when the antimicrobial composition is no longer operating at its full capacity. In this manner, the user can initially wear the article without fear of infection. After a certain period of time, the user can visually inspect the color of the pH sensor to obtain an indication of whether the antimicrobial composition is still active and effective in inhibiting microorganism growth, or whether it is time to replace or remove the article. Various embodiments of the present invention will now be described in more detail.

I. Antimicrobial Composition

The antimicrobial composition generally contains one or more antimicrobial agents. At least one of the agents is an acidic compound that can help maintain an acidic pH and thus inhibit the growth of pathogens in the vagina, whose growth is normally suppressed by lactobacilli and the acidic pH of the vagina. The acid may be generally considered "weak" so that it may safely contact the skin of a user, but yet strong enough to achieve the desired pH level. In this regard, the acid typically has a first acid dissociation constant ($pK_{a1}$) of about 0 to about 8, in some embodiments about 0.5 to about 6, and in some embodiments, from about 1 to about 5, determined at 25° C. This may result in a pH level for the antimicrobial composition of 7 or less, in some embodiments from about 1 to about 6, and in some embodiments, from about 2 to about 5.

Particularly suitable acidic compounds having these characteristics are carboxylic acids, such as aliphatic carboxylic acids, aromatic carboxylic acids, aliphatic-aromatic carboxylic acids, etc., as well as combination thereof. Suitable aliphatic carboxylic acids may include, for instance, acrylic acid, methacrylic acid, malonic acid, succinic acid, adipic acid, maleic acid, malic acid, oleic acid, tartaric acid (e.g., dextotartaric acid, mesotartaric acid, etc.), citric acid, formic acid, acetic acid, glycolic acid, oxalic acid, propionic acid, glutaric acid, gluconic acid, lactic acid, aspartic acid, glutaminic acid, itaconic acid, trifluoroacetic acid, etc. Suitable aromatic carboxylic acids may include, for instance, benzoic acid, trihydroxybenzoic acid (i.e., gallic acid), salicylic acid, terephthalic acid, isophthalic acid, etc. Polymeric acids, such as poly(acrylic) or poly(methacrylic) acid and copolymers thereof (e.g., maleic-acrylic, sulfonic-acrylic, and styrene-acrylic copolymers), may also be suitable for use in the present invention. Particularly suitable acids are polyprotic acids (e.g., diprotic, triprotic, etc.), such as α-tartaric acid ($pk_{a1}$ of 2.98 and $pK_{a2}$ of 4.34 at 25° C.), maleic acid ($pk_{a1}$ of 1.92 and $pK_{a2}$ of 6.27 at 25° C.), oxalic acid ($pK_{a1}$ of 1.23 and $pK_{a2}$ of 4.19 at 25° C.), citric acid ($pK_{a1}$ of 3.13, $pK_{a2}$ of 4.76, and $pK_{a3}$ of 6.40 at 25° C.), etc.

In addition to acidic compounds that can help inhibit microbe growth by maintaining a low vaginal pH level, conventional biocides may also be employed in the composition that actively kill microorganisms, Suitable biocides may include, for instance, phenolic compounds, such as p-chlorornetaxylenol ("PCMX"), 2,4,4'-trichloro-2 hydroxy di-phenyl ether ("triclosan"), 2-chlorophenol, 3-chlorophenol, 4-chlorophenol, 2,4-dichlorophenol, 2,4,6-trichlorophenol, 2,3,4,6-tetrachlorophenol, pentachlorophenol, 4-chlororesorcinol, 4,6-dichlororesorcinol, 2,4,6-trichlororesorcinol, alkylchlorophenols (including p-alkyl-o-chlorophenols, o-alkyl-p-chlorophenols, dialkyl-4-chlorophenol, and tri-alkyl-4-chlorophenol), dichloro-m-xylenol, chlorocresol, o-benzyl-p-chlorophenol, 3,4,6-trichlorphenol, 4-chloro-2-phenylphenol, 6-chloro-2-phenylphenol, o-benzyl-p-chlorophenol, and 2,4-dichloro-3,5-diethylphenol; biguanide compounds, such as chlorhexidine, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine diiodobutyrate, chlorhexidine di-n-valerate, chlorhexidine dicaproate, chlorhexidine malonate, chlorhexidine succinate, chlorhexidine malate, chlorhexidine tartrate, chlorhexidine gluconate ("CHG"), techlorhexidine dimonoglycolate, chlorhexidine monodiglycolate, chlorhexidine dilactate, chlorhexidine di.alpha.-hydroxy-isobutyrate, chlorhexidine diglucoheptonate, chlorhexidine diisothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, polyhexamethylene biguanide ("PHMB"), and alexidine (N,N"-bis(2-ethylhexyl)-3,12-diimino-2,4,11,13-tetraazatetradecanediimid-amine; 1,1'-hexamethyl-enebis[5-(2-ethylhexyl)biguanide]); quaternary ammonium compounds, such as behenalkonium chloride, cetalkonium chloride, cetarylalkonium bromide, cetrimonium tosylate, cetyl pyridinium chloride, lauralkonium bromide, lauralkonium chloride, lapyrium chloride, lauryl pyridinium chloride, myristalkonium chloride, olealkonium chloride, isostearyl ethyldimonium chloride; and so forth, as well as mixtures thereof.

While biocides may certainly be employed, it is normally desired that the amount of such ingredients is minimized to avoid disrupting the natural balance of lactobacilli found in the vagina. Thus, biocides typically constitute only about 20 wt. % or less, in some embodiments about 10 wt. % or less, and in some embodiments, from about 0.001 wt. % to about 5 wt. % of antimicrobial agents employed in the antimicrobial composition, on a dry basis. To the contrary, the aforementioned acidic compounds typically constitute a majority of antimicrobial agents employed in the antimicrobial composition, such as from about 50 wt. % to 100 wt. %, in some embodiments from about 60 wt. % to about 99 wt. %, and in some embodiments, from about 70 wt. % to about 95 wt. % on a dry basis.

If desired, the antimicrobial composition may optionally include additional ingredients to impart various benefits. For instance, the antimicrobial composition may contain one or more surfactants to enhance the wettability of the composition, help emulsify or dissolve other ingredients, increase viscosity, etc. Suitable surfactants may include, for instance, cationic surfactants, anionic surfactants, nonionic surfactants, zwitterionic surfactants, and combinations thereof. When utilized, the amount of the surfactants utilized in the antimicrobial composition may generally vary depending on the relative amounts of the other components present within the composition. The antimicrobial composition may also contain a preservative or preservative system to help further inhibit the growth of microorganisms over an extended period of time. Suitable preservatives may include, for instance, alkanols, disodium EDTA (ethylenediamine tetraacetate), EDTA salts, EDTA fatty acid conjugates, isothiazolinone, benzoic esters (parabens) (e.g., methylparaben, propylparaben, butylparaben, ethylparaben, isopropylparaben, isobutylparaben, benzylparaben, sodium methylparaben, and sodium propylparaben), and so forth.

II. pH Sensor

As noted above, the antimicrobial composition has an initial pH level of less than about 7, in some embodiments from about 1 to about 6, and in some embodiments, from about 2 to about 5 due to the presence of acidic compounds therein. This low pH level can help minimize the growth of microorganisms within the feminine care absorbent article and/or vagina. Bodily fluids (e.g., perspiration, urine, etc.), however, typically have a relatively high pH, such as about 7 or even greater. Thus, when the article absorbs a sufficient amount of bodily fluid, the antimicrobial composition may no longer be able to keep the overall pH at a low enough level to inhibit microorganism growth. In this regard, the feminine care absorbent article of the present invention also employs a pH sensor that is able to signal to the user that the antimicrobial composition has lost or is beginning to lose its optimal efficacy. The pH sensor may also serve to indicate the presence of the bodily fluid itself (e.g., perspiration). This is particularly useful in, for example, warm environments in which a user may secrete a significant amount of perspiration. In addition to reducing the efficacy of the antimicrobial composition, the perspiration can also act as a carrier for microorganisms.

To accomplish the desired functions, the sensor includes a pH-sensitive composition that undergoes a change in color at a pH level at which it is believed that the antimicrobial composition will no longer possess optimal efficacy. For example, the pH level at which the color transition occurs may be from about 3 to about 9, in some embodiments from about 4 to about 8, and in some embodiments, from about 5 to about 7, and in one embodiment, about 7. The pH-sensitive composition may, for instance, exhibit a first color at pH values of less than about 9, in some embodiments less than about 8, in some embodiments less than about 7, in some embodiments less than about 6, in some embodiments less than about 5, and in some embodiments, less than about 4. Likewise, the pH-sensitive composition may also exhibit a second color at pH values of about 4 or more, in some embodiments about 5 or more, in some embodiments about 6 or more, in some embodiments about 7 or more, in some embodiments about 8 or more, and in some embodiments, about 9 or more. The first color may be present when the composition is in its dry state, and the second color may be present when the composition comes into contact with the bodily fluid. It should be noted that the term "color" as used herein include a composition that is generally clear or colorless.

The pH-sensitive composition employs one or more chromogens to achieve the desired color change. The particular chromogens employed in the pH-sensitive composition are not generally critical. For instance, phthalein chromogens constitute one class of suitable pH-sensitive chromogens that may be employed in the present disclosure. Phenol Red (i.e., phenolsulfonephthalein), for example, exhibits a transition from yellow to red over the pH range 6.6 to 8.0. Above a pH of about 8.1, Phenol Red turns a bright pink (fuchsia) color. Derivatives of Phenol Red can also be suitable for use in the present disclosure, such as those substituted with chloro, bromo, methyl, sodium carboxylate, carboxylic acid, hydroxyl and amine functional groups. Exemplary substituted Phenol Red compounds include, for instance, Meta-cresol Purple (meta-cresolsulfonephthalein), Cresol Red (ortho-cresolsulfonephthalein), Pyrocatecol Violet (pyrocatecolsulfonephthalein), Chlorophenol Red (3',3"-dichlorophenolsulfonephthalein), Xylenol Blue (the sodium salt of para-xylenolsulfonephthalein), Xylenol Orange, Mordant Blue 3 (C.I. 43820), 3,4,5,6-tetrabromophenolsulfonephthalein, Bromoxylenol Blue, Bromophenol Blue (3',", 5',5"-tetrabromophenolsulfonephthalein), Bromiochlorophenol Blue (the sodium salt of dibromo-5',5"-dichlorophenolsulfonephthalein), Bromocresol Purple (5',5"-dibromo-ortho-cresolsulfonephthalein), Bromocresol Green (3',", 5',5"-tetrabromo-ortho-cresolsuffonephthalein), and so forth. For example, Bromocresol Green exhibits a transition from yellow to blue over a pH range of about 4 to about 6; Bromothymol Blue exhibits a transition from yellow to blue over a pH range of about 6.0 to 7.6; Bromophenol Blue exhibits a transition from yellow to violet over a pH range of about 3.0 to 4.6; and Bromocresol Purple exhibits a transition from yellow to violet over a pH of about 5.2 to 6.8.

Anthraquinones constitute another suitable class of pH-sensitive chromogens for use in the present disclosure. Anthraquinones have the following general structure:

The numbers 1-8 shown in the general formula represent a location on the fused ring structure at which substitution of a functional group can occur. Some examples of such functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, hydroxy groups, phosphorous groups, etc. Functional groups that result in an ionizing capability are often referred to as "chromophores." Substitution of the ring structure with a chromophore causes a shift in the absorbance wavelength of the compound. Thus, depending on the type of chromophore (e.g., hydroxyl, carboxyl, amino, etc.) and the extent of substitution, a wide variety of quinones may be formed with varying colors and intensities. Other functional groups, such as sulfonic acids, can also be used to render certain types of compounds (e.g., higher molecular weight anthraquinones) water-soluble.

Some suitable anthraquinones that may be used in the present disclosure, as classified by their "CI" number, include Acid Black 48, Acid Blue 25 (D&C Green No. 5), Acid Blue 40, Acid Blue 41, Acid Blue 45, Acid Blue 80, Acid Blue 129, Acid Green 25, Acid Green 27, Acid Green 41, Acid Violet 43, Mordant Red 11 (Alizarin), Mordant Black 13 (Alizarin Blue Black B), Mordant Red 3 (Alizarin Red S), Mordant Violet 5 (Alizarin Violet 3R), Alizarin Complexone, Natural Red 4 (Carminic Acid), Disperse Blue 1, Disperse Blue 3, Disperse Blue 14, Natural Red 16 (Purpurin), Natural Red 8, Reactive Blue 2 (Procion Blue HB), Reactive Blue 19 (Remazol Brilliant Blue R); Alizarin, Alizarin Yellow R, Alizarin Yellow GG, Alizarin S, Nuclear Fast Red, Quinalizarin, Emodin, amino-4-hydroxyanthraquinone, and so forth. For instance, carminic acid exhibits a first transition from orange to red over a pH range of about 3.0 to 5.5 and a second transition from red to purple over a pH range of about 5.5 to 7.0.

Yet another suitable class of pH-sensitive chromogens that may be employed is aromatic azo compounds having the general structure:

wherein, $R_1$ is an aromatic group;

$R_2$ is selected from the group consisting of aliphatic and aromatic groups; and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, halides, etc. Also suitable are azo derivatives, such as azoxy compounds (X—$R_1$—N=NO—$R_2$—Y) or hydrazo compounds (X—$R_1$—NH—NH—$R_2$—Y). Particular examples of such azo compounds (or derivatives thereof) include Methyl Violet, Methyl Yellow, Methyl Orange, Methyl Red, and Methyl Green. For instance, Methyl Yellow undergoes a transition from red to yellow at a pH range of about 2.9 to 4.0, Methyl Orange undergoes a transition from red to yellow at a pH range of about 3.1 to 4.4, and Methyl Red undergoes a transition from red to yellow at a pH range of about 4.2 to 6.3.

Arylmethanes (e.g., diarylmethanes and triarylmethanes) constitute still another class of suitable pH-sensitive chromogens for use in the present disclosure. Triarylmethane leuco bases, for example, have the following general structure:

wherein R, R', and R" are independently selected from substituted and unsubstituted aryl groups, such as phenyl, naphthyl, anthracenyl, etc. The aryl groups may be substituted with functional groups, such as amino, hydroxyl, carbonyl, carboxyl, sulfonic, alkyl, and/or other known functional groups. Examples of such triarylmethane leuco bases include Leucomalachite Green, Pararosaniline Base, Crystal Violet Lactone, Crystal Violet Leuco, Crystal Violet, CI Basic Violet 1, CI Basic Violet 2, CI Basic Blue, CI Victoria Blue, N-benzoyl leuco-methylene, etc. Likewise suitable diarylmethane leuco bases can include 4,4'-bis(dimethylamino) benzhydrol (also known as "Michler's hydrol"), Michler's hydrol leucobenzotriazole, Michler's hydrol leucomorpholine, Michler's hydrol leucobenzenesulfonamide, etc.

Still other suitable pH-sensitive chromogens that may be employed include Congo Red, Litmus (azolitmin), Methylene Blue, Neutral Red, Acid Fuchsin, Indigo Carmine, Brilliant Green, Picric acid, Metanil Yellow, m-Cresol Purple, Quinaldine Red, Tropaeolin OO, 2,6-dinitrophenol, Phloxine B, 2,4-dinitrophenol, 4-dimethylaminoazobenzene, 2,5-dinitrophenol, 1-Naphthyl Red, Chlorophenol Red, Hematoxylin, 4-nitrophenol, nitrazine yellow, 3-nitrophenol, Alkali Blue, Epsilon Blue, Nile Blue A, universal chromogens, and so forth. For instance, Congo Red undergoes a transition from blue to red at a pH range of about 3.0 to 5.2 and Litmus undergoes a transition from red to blue at a pH range of about 4.5 to 8.3.

Although the overall amount may vary, the pH chromogen(s) typically constitute from about 0.01 wt. % to about 15 wt. %, in some embodiments from about 0.1 wt. % to about 5 wt. %, and in some embodiments, from about 0.2 wt. % to about 1 wt. %, of the pH-sensitive composition on a dry basis.

Of course, the pH-sensitive composition may also contain a variety of optional components to facilitate the desired color change, and also to enhance the ability of the composition to remain stable on a substrate of the feminine care absorbent article to which it is applied. Organic binders may, for instance, be employed to increase the durability of the pH-sensitive composition and help form stable films on various substrates upon drying. Because the composition is intended for contact with aqueous bodily fluids (e.g., urine), it is sometimes desired that hydrophobic organic binders are employed. One example of such a binder is a thermoset resin that is capable of hardening upon application to the substrate. Suitable thermoset resins may include, for instance, polyester resins, polyurethane resins, melamine resins, epoxy resins, diallyl phthalate resins, vinylester resins, and so forth. In addition or in conjunction with such hydrophobic binders, the composition may also contain a hydrophilic binder, such as alginic acid and salts thereof, carrageenan, pectin, gelatin and the like, semisynthetic macromolecular compounds, such as methylcellulose, cationized starch, carboxymethylcellulose, carboxymethylated starch, nitrocellulose, vinyl polymers (e.g., polyvinyl alcohol), polyvinylpyrrolidone, polyacrylic acid, polyacrylamide, maleic acid copolymers, cellulose acetate, cellulose butyrate, etc., as well as combination thereof. Commercially available binder systems that may be employed include, for instance, the GANTREZ® SP, ES, or AN series of monoalkyl esters of poly(methyl vinyl ether/maleic acid) (International Specialty Products, Inc.), the DERMACRYL® series of carboxylated acrylic copolymers (Akzo Nobel), and the AMPHOMER® series of amphoteric acrylic copolymers (Akzo Nobel).

The total concentration of binders may generally vary depending on the desired properties of the resulting substrate. For instance, high total binder concentrations may provide better physical properties for the coated substrate, but may likewise have an adverse affect on other properties, such as the absorptive capacity of the substrate to which it is applied. Conversely, low total binder concentrations may not provide the desired degree of durability. In most embodiments, however, the total amount of binder employed in the composition, including any hydrophilic or hydrophobic binders, is from about 20 wt. % to about 90 wt. %, in some embodiments from about 40 wt. % to about 85 wt. %, and in some embodiments, from about 60 wt. % to about 80 wt. %, on a dry weight basis.

The pH-sensitive composition may also contain other components as is known in the art. For example, a wetting agent may sometimes be employed to improve the ability to apply and adhere the pH-sensitive composition to a substrate. Suitable wetting agents may include, for instance, a surfactant (e.g., nonionic, cationic, anionic, or zwitterionic) or a mixture of surfactants. The surfactants may also help enhance the sensitivity and contrast provided by the colorant. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11}$-$C_{15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa. Cationic surfactants may also be employed in the present invention, such as quaternary ammonium compounds (e.g., cetyl trimethyl ammonium chloride, benzalkonium chloride, benzethonium chloride, quaternium-18, stearalkonium chloride, cocotrimonium methosulfate, PEG-2 cocomonium chloride, and PEG-3 dioleoylamidoethylmonium methosulfate, etc). In certain embodiments, such cationic surfactants may also aid in adhering the composition to a substrate having a negatively charged surface, such as films and/or nonwoven webs formed from olefinic polymers. When employed, such wetting agents typically constitute from about 0.01 wt. % to about 20 wt. %, in some embodiments from about 0.1 wt. % to about an about 15 wt. %, and in some embodiments, from about 1 wt. % to about 10 wt. % of the composition.

The initial pH of the composition may also be controlled within a certain range to ensure that it exhibits a first color before use of the article, and then undergoes a color change upon contact with a bodily fluid. The pH may also be low enough so that humidity from the environment alone (e.g., in storage or use) does not induce the color change. For instance, it is typically desired that the initial pH of the composition is within a range of from about 3 to about 6, and in some embodiments, from about 4 to about 6. Various pH modifiers may be employed to achieve the desired pH level. Some examples of pH modifiers that may be used in the present invention include, but are not limited to, mineral acids, sulfonic acids (e.g., 2-[N-morpholino]ethane sulfonic acid), carboxylic acids, and polymeric acids. Specific examples of suitable mineral acids are hydrochloric acid, nitric acid, phosphoric acid, and sulfuric acid. Specific examples of suitable carboxylic acids are lactic acid, acetic acid, citric acid, glycolic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, carboxymethyl cellulose, and alginic acid. While the amount of pH modifiers will generally depend on the desired pH level, such components typically constitute from about 1 wt. % to about 40 wt. %, in some embodiments from about 5 wt. % to about 30 wt. %, and in some embodiments, from about 10 wt. % to about 25 wt. % of the composition.

Humectants may also be utilized, such as ethylene glycol; diethylene glycol; glycerine; polyethylene glycol 200, 300, 400, and 600; propane 1,3diol; propylene-glycolmonomethyl ethers, such as Dowanol PM (Gallade Chemical Inc., Santa Ana, Calif.); polyhydric alcohols; or combinations thereof. Further, additional pH-insensitive chromogens may also be employed to help control the color that is observed during use of the pH-sensitive composition. Other additives may also be included to improve performance, such as a chelating agent to sequester metal ions that could become involved in chemical reactions over time and/or a corrosion inhibitor to help protect metal components of the printer or ink delivery system. Various other components may also be employed, such as colorant stabilizers, photoinitiators, fillers, etc., such as described in U.S. Pat. Nos. 5,681,380 to Nohr, et al. and 6,542,379 to Nohr, et al., which are incorporated herein in their entirety by reference thereto for all purposes.

The pH sensor of the present invention may be defined by the pH-sensitive composition itself, such as when it is directly applied to a component of the absorbent article. Alternatively, the pH sensor may include a separate substrate on which the pH-sensitive composition is disposed. Examples of such substrates include, for instance, nonwoven webs, woven fabrics, knit fabrics, paper webs, films, foams, strands, etc. Nonwoven webs may include, but are not limited to, spunbonded webs (apertured or non-apertured), meltblown webs, bonded carded webs, air-laid webs, coform webs, hydraulically entangled webs, and so forth. Nonwoven composites (e.g., nonwoven web laminated to a film or strands) may also be employed. Examples of polymers for forming such webs may include, but are not limited to, synthetic polymers (e.g., polyethylene, polypropylene, polyethylene terephthalate, nylon 6, nylon 66, KEVLAR®), syndiotactic polystyrene, liquid crystalline polyesters, etc.); cellulosic polymers (softwood pulp, hardwood pulp, thermomechanical pulp, etc.); combinations thereof; and so forth. When the pH-sensitive composition is applied to a separate substrate, it may be subsequently adhered or otherwise attached to a layer of the absorbent article using any known technique. An adhesive, such as a pressure-sensitive adhesive, heat-activated adhesive, hot melt adhesive, etc., may be employed on one or more surfaces of the substrate to help adhere it to a surface of the absorbent article. Suitable examples of pressure-sensitive adhesives include, for instance, acrylic-based adhesives and elastomeric adhesives. In one embodiment, the pressure-sensitive adhesive is based on copolymers of acrylic acid esters (e.g., 2-ethyl hexyl acrylate) with polar co-monomers (e.g., acrylic acid). The adhesive may have a thickness in the range of from about 0.1 to about 2 mils (2.5 to 50 microns).

The pH-sensitive composition may be applied to a substrate (e.g., component of the absorbent article or a separate substrate), either independently from or in conjunction with the antimicrobial composition described above. Typically, the components of the composition are initially dissolved or dispersed in a solvent to form a coating solution. Any solvent capable of dispersing or dissolving the components is suitable. Suitable solvents may include, for instance, water; alcohols, such as ethanol or methanol; dimethylformamide; dimethyl sulfoxide; hydrocarbons, such as pentane, butane, heptane, hexane, toluene and xylene; ethers such as diethyl ether and tetrahydrofuran; ketones and aldehydes, such as acetone and methyl ethyl ketone; halogenated solvents, such as dichloromethane and carbon tetrachloride; acrylonitrile; etc., as well as mixtures thereof. The concentration of solvent in the coating formulation is generally high enough to allow easy application, handling, etc.

When employed, the total concentration of solvent(s) may vary, but is typically from about 1 wt. % to about 95 wt. %, in some embodiments from about 5 wt. % to about 80 wt. %, and in some embodiments, from about 10 wt. % to about 50 wt. % of the coating formulation. A coating formulation may be applied using any conventional technique, such as printing, dipping, spraying, melt extruding, coating (e.g., solvent coating, powder coating, brush coating, etc.), and so forth. In one embodiment, for example, the pH-sensitive composition is printed onto one substrate (e.g., baffle). A variety of printing techniques may be used for applying the composition to the support, such as gravure printing, flexographic printing, screen printing, laser printing, thermal ribbon printing, piston printing, etc. In one particular embodiment, ink-jet printing techniques are employed to apply the composition to the substrate. Ink-jet printing is a non-contact printing technique that involves forcing an ink through a tiny nozzle (or a series of nozzles) to form droplets that are directed toward the support. Two techniques are generally utilized, i.e., "DOD" (prop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

A coating formulation may be applied to one or both surfaces of the substrate. For example, the resulting pH-sensitive composition is generally present on at least the surface of the substrate that is likely to contact bodily fluids during use. In addition, the composition may cover an entire surface of the substrate, or may only cover a portion of the surface. When applying the composition to multiple surfaces, each surface may be coated sequentially or simultaneously. Regardless of the manner in which it is applied, the resulting substrate may be dried at a certain temperature to drive the solvent from the formulation and form the composition of the present invention. For example, the substrate may be dried at a temperature of at least about 20° C., in some embodiments at least about 25° C., and in some embodiments, from about 25° C. to about 75° C.

To maintain absorbency, porosity, flexibility, and/or some other characteristic of the substrate, it may sometimes be desired to apply the composition so as to cover less than 100%, in some embodiments from about 10% to about 80%, and in some embodiments, from about 20% to about 60% of the area of one or more surfaces of the substrate. For instance, in one particular embodiment, the pH-sensitive composition is applied to a substrate in a preselected pattern (e.g., reticular pattern, diamond-shaped grid, dots, and so forth). The pattern may include indicia, such as numerical values, lettering, or graphics that illustrate impending lack of antimicrobial efficacy. It should be understood, however, that the composition may also be applied uniformly to one or more surfaces of the substrate. In addition, a patterned composition may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first composition, while another region is coated with a second composition.

It is generally desired that the pH-sensitive composition is applied in a manner so that it does not substantially diffuse through the substrate (i.e., non-diffusively immobilized). This enables a user to readily detect the change in color that occurs and also prevents the composition from leaching out of the substrate. The immobilization may be achieved by many methods such as chemical bonding (ionic bonding, covalent bonding, etc.), physical absorption, or using a carrier. In one embodiment, for example, a cationic material (e.g., cationic surfactant) is employed to help ionically adhere the composition to a negatively charged substrate material. In other embodiments, an anchoring compound may be employed that links the ink to the surface of substrate and further improves durability. Typically, the anchoring compound is larger in size than the chromogen, which improves their likelihood of remaining on the surface during use. For example, the anchoring compound can include a macromolecular compound, such as a polymer, oligomer, dendrimer, particle, etc. Polymeric anchoring compounds can be natural, synthetic, or combinations thereof. Examples of natural polymeric anchoring compounds include, for instance, polypeptides, proteins, DNA/RNA and polysaccharides (e.g., glucose-based polymers, activated dextran, etc). In some embodiments, the anchoring compound can be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., can be used. Further, synthetic particles can also be utilized. For example, in one embodiment, latex microparticles are utilized. Although any synthetic particle can be used, the particles are typically formed from polystyrene, butadiene styrenes, styreneacrylic-vinyl terpolymer, polymethylmethacrylate, polyethyl methacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the size of the particles may vary. For instance, the average size (e.g., diameter) of the particles can range from about 0.1 nanometers to about 1,000 microns, in some embodiments, from about 0.1 nanometers to about 100 microns, and in some embodiments, from about 1 nanometer to about 10 microns.

Regardless of the manner in which the pH sensor is formed, the resulting color change may be fairly rapid and may be detected within a relatively short period of time. For example, a visual change in color may occur in about 10 minutes or less, in some embodiments about 1 minutes or less, and in some embodiments, from about 0.1 to about 60 seconds. The extent of the color change is also generally sufficient to provide a "real-time" indication of antimicrobial effectiveness. This color change may, for example, be represented by a certain change in the absorbance reading as measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, $L^*$, $a^*$, and $b^*$, which correspond to three characteristics of a perceived color based on the opponent theory of color perception. The three variables have the following meaning:

$L^*$=Lightness (or luminosity), ranging from 0 to 100, where 0=dark and 100=light;

$a^*$=Red/green axis, ranging approximately from −100 to 100; positive values are reddish and negative values are greenish; and $b^*$=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed $\Delta E$ and calculated by taking the square root of the sum of the squares of the three differences ($\Delta L^*$, $\Delta a^*$, and $\Delta b^*$) between the two colors. In CIELAB color space, each $\Delta E$ unit is approximately equal to a "just noticeable" difference between two colors. CIELAB is therefore a good measure for an objective device-independent color specification system that may be used as a reference color space for the purpose of color management and expression of changes in color. Using this test, color intensities ($L^*$, $a^*$, and $b^*$) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS 28722-1982 (diffused illumination/8-degree viewing system. The D65 fight reflected by the specimen surface at an angle of 8 degrees to the normal of the surface is received by the specimen-measuring optical system. Typically, the color change is represented by a $\Delta E$ of about 2 or more, in some embodiments about 3 or more, and in some embodiments, from about 5 to about 50.

The pH sensor may also be able to maintain its signal strength (i.e., change in color) for a long enough period of time to ensure that the user is able to detect the change in appearance. For example, the pH sensor may be able to maintain signal strength for at least about 10 minutes, in some embodiments at least about 30 minutes, and in some embodiments, at least about 1 hour. Additionally, the sensor may be subjected to multiple urine insults and still produce accurate test results.

It should be understood that all of the application techniques and methods, coating formulations, etc. referenced above with respect to the pH-sensitive composition are equally applicable to the antimicrobial composition. For example, the antimicrobial agents may be formed into a coating formulation and applied to a substrate or component of the absorbent article using any of the techniques referenced herein. The composition may be uniformly or non-uniformly applied to the substrate or component of the absorbent article.

III. Absorbent Article

The feminine care absorbent article of the present invention includes at least one generally liquid-impermeable layer (e.g., outer cover or baffle), at least one liquid-permeable layer (e.g., topsheet, intake layer, transfer delay layer, etc.), and an absorbent core positioned between a liquid-impermeable layer and liquid-permeable layer. The antimicrobial composition and pH sensor of the present invention may generally be disposed in fluid communication with any of these components in a variety of different orientations and configurations. Nevertheless, in most embodiments, it is desired that the pH sensor is applied to a layer of the article where it can be easily seen by the user, such as a liquid-impermeable layer, and that the antimicrobial composition is located on a liquid-permeable layer so that it is in close proximity to the user's body and best inhibit the growth of pathogens. The antimicrobial composition and pH sensor may be applied directly to a component of the article or via a substrate as described above.

Figure 1:
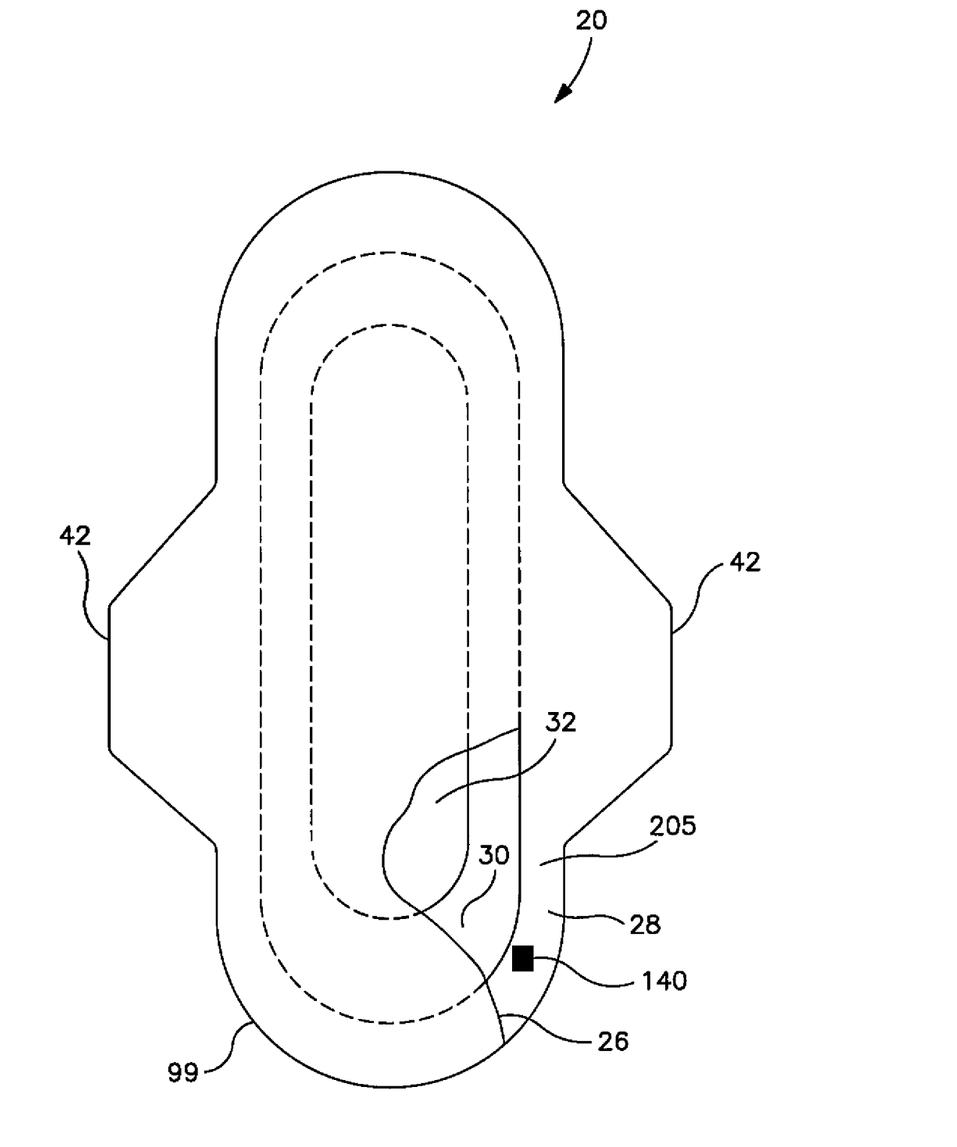
FIG. 1 is a top view of one embodiment of the feminine care absorbent article of the present invention.

Referring to FIG. 1, one particular embodiment of a feminine care absorbent article 20 will now be described in more detail. More particularly, the article 20 includes a topsheet 26, a baffle 28, and an absorbent core 30 positioned between the topsheet 26 and the baffle 28. The topsheet 26 defines a body-facing surface 27 of the absorbent article 20. The absorbent core 30 is positioned inwardly from the outer periphery of the absorbent article 20 and includes a body-facing side positioned adjacent the topsheet 26 and a garment-facing surface positioned adjacent the baffle 28. Typically, the topsheet 26 and the baffle 28 are joined by adhesive bonding, ultrasonic bonding, or any other suitable joining method known in the art, the sealed edges defining an overall sealed peripheral edge 99 of the article 20. The article 20 may take on various geometries but will generally have opposite lateral sides and longitudinal ends.

The topsheet 26 is generally designed to contact the body of the user and is liquid-permeable. The liquid permeable topsheet 26 has an outwardly facing surface that may contact the body of the user and receive aqueous fluids from the body. The topsheet 26 is provided for comfort and conformability and functions to direct bodily exudates away from the body, through the topsheet 26 and toward the absorbent core 30. The topsheet 26 retains little or no liquid in its structure so that it provides a relatively comfortable and non-irritating surface next to the tissues within the vestibule of a female user. The topsheet 26 may be constructed of any woven or nonwoven material that is easily penetrated by bodily exudates contacting the surface of the baffle. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable topsheet material is a bonded carded web made of polypropylene and polyethylene such as that used as topsheet stock for KOTEX® pantiliners and obtainable from Sandler Corporation (Germany). U.S. Pat. Nos. 4,801,494 to Datta, et al. and 4,908,026 to Sukiennik, et al. teach various other topsheet materials that may be used in the present invention. The topsheet 26 may also contain a plurality of apertures (not shown) formed therethrough to permit body fluid to pass more readily into the absorbent core 30. The apertures may be randomly or uniformly arranged throughout the topsheet 26, or they may be located only in the narrow longitudinal band or strip arranged along the longitudinal axis of the absorbent article 20. The apertures permit rapid penetration of body fluid down into the absorbent core 30. The size, shape, diameter and number of apertures may be varied to suit one's particular needs.

The baffle 28 is generally liquid-impermeable and designed to face the inner surface, i.e., the crotch portion of an undergarment (not shown). The baffle 28 may permit a passage of air or vapor out of the absorbent article 20, while still blocking the passage of liquids. Any liquid-impermeable material may generally be utilized to form the baffle 28. For example, one suitable material that may be utilized is a microporous polymeric film, such as polyethylene or polypropylene. In particular embodiments, a polyethylene film is utilized that has a thickness in the range of about 0.2 mils to about 5.0 mils, and particularly between about 0.5 to about 3.0 mils. A specific example of a baffle material is a polyethylene film such as that used in KOTEX® pantiliners and obtainable from Pliant Corporation, Schaumburg, Ill., USA.

As indicated above, an absorbent core 30 is positioned between the topsheet 26 and the baffle 28 that provides capacity to absorb and retain bodily exudates. The absorbent core 30 may be formed from a variety of different materials and contain any number of desired layers. For example, the core 30 typically includes one or more layers of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

The topsheet 26 may be maintained in secured relation with the absorbent core 30 by bonding all or a portion of the adjacent surfaces to one another. A variety of bonding mechanisms known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent. The topsheet 26 typically extends over the upper, bodyside surface of the absorbent core 30, but can alternatively extend around the article to partially or entirely, surround or enclose the absorbent core. Alternatively, the topsheet 26 and the baffle 28 can have peripheral margins that extend outwardly beyond the terminal, peripheral edges of the absorbent core 30, and the extending margins may be joined together to partially or entirely, surround or enclose the absorbent core.

Although not required, the absorbent article 20 may also contain other additional layers as is known in the art. In FIG. 1, for example, a liquid-permeable intake layer 32 is positioned vertically between the topsheet 26 and the absorbent core 30. The intake layer 32 may be made of a material that is capable of rapidly transferring, in the z-direction, body fluid that is delivered to the topsheet 26. The intake layer 32 may generally have any shape and/or size desired. In one embodiment, the intake layer 32 has a rectangular shape, with a length equal to or less than the overall length of the absorbent article 20, and a width less than the width of the absorbent article 20. For example, a length of between about 150 mm to about 300 mm and a width of between about 10 mm to about 60 mm may be utilized. Any of a variety of different materials may be used for the intake layer 32 to accomplish the above-mentioned functions. The material may be synthetic, cellulosic, or a combination of synthetic and cellulosic materials. For example, airlaid cellulosic tissues may be suitable for use in the intake layer 32. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The absorbent article 20 may also contain a transfer delay layer (not shown) positioned between the intake layer 32 and the absorbent core 30. The transfer delay layer may contain a material that is substantially hydrophobic, such as a nonwoven web composed of polypropylene, polyethylene, polyester, etc. One example of a material suitable for the transfer delay layer is a spunbond web composed of polypropylene, multi-lobal fibers. Further examples of suitable transfer delay layer materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer 36 are described in U.S. Pat. Nos. 4,798,603 to Meyer, et al. and 5,248,309 to Serbiak, et al. To adjust performance, the transfer delay layer may also be treated with a selected amount of surfactant to increase its initial wettability. The transfer delay layer typically has a basis weight less than that of the other absorbent members. For example, the basis weight of the transfer delay layer 36 is typically less than about 250 grams per square meter (gsm), and in some embodiments, between about 40 gsm to about 200 gsm.

The absorbent article 20 may also include laterally extending wing portions 42 that may be integrally connected to side regions along the intermediate portion of the article. For example, the wing portions 42 may be separately provided members that are subsequently attached or otherwise operatively joined to the intermediate portion of the article. In other configurations, the wing portions may be unitarily formed with one or more components of the article. As representatively shown in FIG. 1, for example, either or both wing portions 42 may be formed from a corresponding, operative extension of the material employed to form the topsheet 26. Alternatively, either or both wing portions 42 may be formed from a corresponding, operative extension of the material employed to form the baffle 28, or formed from a corresponding, operative combination of the topsheet and baffle materials.

As indicated above, the antimicrobial composition and pH sensor may be disposed on any layer of the absorbent article 20 desired. In certain embodiments, however, the antimicrobial composition is located on a liquid-permeable layer of the absorbent article (e.g., topsheet, intake layer, transfer delay layer, etc.) so it is in close proximity to the user's body. In the embodiment shown in FIG. 1, for example, the antimicrobial composition (not shown) may be applied to the topsheet 26 (e.g., uniformly or non-uniformly). The resulting pH of the topsheet 26 is thus typically less than about 7, and in some embodiments, from about 5 to about 6. The pH sensor is likewise typically applied to a layer of the article where it can be easily seen by the user. In FIG. 1, for instance, the pH sensor is shown as element 140 and is applied to a body-facing surface 205 of the baffle 28, such as adjacent to a nonwoven web or film of a composite used to form the baffle. If desired, a transparent or translucent portion (e.g., window, film, etc.) may be employed to allow the pH-sensitive composition 140 to be readily viewed without removal of the absorbent article from the user and/or without disassembly. In other embodiments, the pH-sensitive composition 140 can be seen through a hole or aperture in the absorbent article for observation.

If desired, a plurality of pH sensors may also be employed to ensure that the signal is adequately conveyed to the user. For example, in certain embodiments, 2 sensors may be utilized. In still other embodiments, 3 sensors may be utilized, while in still other embodiments, greater than 3 sensors may be utilized. The sensors can form either a straight line, a wave, or a curved line (e.g., parabolic). When multiple sensors are employed, they may optionally be arranged in a pattern (e.g., numbers, letters, graphics, etc.) that better illustrates the impending lack of antimicrobial efficacy.

The present invention may be better understood with reference to the following example.

EXAMPLE

A composition was prepared that contained approximately 70 wt. % of a nitrocellulose-based varnish (SunChemical), 0.5 wt. % of Bromocresol Green, 10.5 wt. % of ethanol, 4 wt. % of benzethonium chloride, 10 wt. % of citric acid, and 5 wt. % of polyacrylic acid. The pH-sensitive composition was applied to the body-facing surface of the baffle of a KOTEX® pad (available from Kimberly-Clark Taiwan) and allowed to air dry. It was observed that the color of the pH-sensitive composition was yellow, indicating acidity. 2 milliliters of synthetic mucus (pH of 7.0) was applied to the left side of the inked area and allowed to spread to the right side of the inked area. It was thereafter observed that the pH-sensitive composition turned blue in color in the area where the mucus was applied, suggesting that the pH of the area was higher than 5.5. The areas where the mucus was not applied remained yellow/green in color. This test confirmed that the pH sensor can be employed in a feminine care absorbent article that uses an antimicrobial composition as described herein. In one embodiment, for example, an aqueous solution of an acidic compound (e.g., maleic acid or lactic acid) may be uniformly applied to the topsheet of a KOTEX® pad (available from Kimberly-Clark Taiwan) and allowed to dry to form the antimicrobial composition. The resulting pH of the topsheet may be about 5.5.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A feminine care absorbent article comprising;
a generally liquid-impermeable layer;
a liquid-permeable layer;
an absorbent core positioned between the generally liquid-impermeable layer and the liquid-permeable layer;
an antimicrobial composition that is uniformly disposed on the liquid-permeable layer, wherein the antimicrobial composition comprises an acidic compound, wherein the acidic compound is a weak organic carboxylic acid; and
a sensor that comprises a pH-sensitive composition, wherein the sensor is integrated into the article and positioned such that the pH-sensitive composition is in fluid communication with a bodily fluid from a user of the feminine care absorbent article, wherein the pH-sensitive composition includes a chromogen that undergoes a visible color change upon contact with the bodily fluid, the visible color change occurring at a pH level of from 3 to 9 so that the pH-sensitive composition exhibits a first color at pH levels of less than 3 and a second color at pH levels of 9 or more, and wherein the pH-sensitive composition further includes an organic hydrophilic binder present in an amount ranging from 40 wt.% to 85 wt.% based on a dry weight of the pH-sensitive composition, wherein the presence of the second color signals to the user whether the antimicrobial composition is effective in inhibiting microorganism growth or is beginning to lose or has lost its efficacy.

2. The feminine care absorbent article of claim 1, wherein the acidic compound is an aliphatic carboxylic acid having a first acid dissociation constant of 0.5 to 6.

3. The feminine care absorbent article of claim 1, wherein the visible color change occurs at a pH level of from 4 to 8.

4. The feminine care absorbent article of claim 1, wherein the chromogen is a phthalein, anthraquinone, aromatic azo, arylmethane, or a combination thereof.

5. The feminine care absorbent article of claim 1, wherein the chromogen is a pthalein chromogen.

6. The feminine care absorbent article of claim 1, wherein the pH-sensitive composition has a pH of from 4 to 6 prior to use of the feminine care absorbent article.

7. The feminine care absorbent article of claim 1, wherein the sensor includes a substrate on which the pH-sensitive composition is disposed.

8. The feminine care absorbent article of claim 1, wherein the sensor is disposed on the generally liquid-impermeable layer.

9. A feminine care absorbent article comprising:
a baffle;
a topsheet;
an absorbent core positioned between the baffle and the topsheet;
an antimicrobial composition that is uniformly disposed on the topsheet, wherein the antimicrobial composition comprises an acidic compound, wherein the acidic compound is a weak organic carboxylic acid; and
a sensor that comprises a pH-sensitive composition, wherein the sensor is disposed on the baffle such that the pH-sensitive composition is in fluid communication with a bodily fluid from a user of the feminine care absorbent article, wherein the pH-sensitive composition includes a chromogen that undergoes a visible color change upon contact with the bodily fluid, the visible color change occurring at a pH level of from 3 to 9 so that the pH sensitive composition exhibits a first color at pH levels of less than 3 and a second color at pH levels of 9 or more, and wherein the pH-sensitive composition further includes an organic hydrophilic binder present in an amount ranging from 40 wt.% to 85 wt.% based on a dry weight of the pH-sensitive composition, wherein the presence of the second color signals to the user whether the antimicrobial composition is effective in inhibiting microorganism growth or is beginning to lose or has lost its efficacy.

10. The feminine care absorbent article of claim 9, wherein the visible color change occurs at a pH level of from 4 to 8.

11. A method for determining when to remove a feminine care absorbent article from a wearer, wherein the feminine care absorbent article comprises an antimicrobial composition and a sensor, the antimicrobial composition being uniformly disposed on the feminine care absorbent article and comprising an acidic compound, wherein the acidic compound is a weak organic carboxylic acid, and the sensor comprising a pH-sensitive composition, wherein the pH-sensitive composition includes a chromogen that undergoes a visible color change within a pH range of from 3 to 9 so that the pH-sensitive composition exhibits a first color at pH values of less than 3 and a second color at pH values of 9 or more, and wherein the pH-sensitive composition further includes an organic hydrophilic binder present in an amount ranging from 40 wt.% to 85 wt.% based on a dry weight of the pH-sensitive composition, wherein the method comprises visually observing the sensor to determine whether the pH sensitive composition has the second color, wherein presence of the second color is indicative of a need to remove the feminine care absorbent article, wherein the second color signals to the wearer that the antimicrobial composition is beginning to lose or has lost its efficacy.

12. The method of claim 11, wherein the visible color change occurs at a pH level of from 4 to 8 so that the pH-sensitive composition exhibits the first color at pH values of 4 or less and the second color at pH values of 8 or more.

13. The method of claim 11, wherein the chromogen is a phthalein, anthraquinone, aromatic azo, arylmethane, or a combination thereof.

14. The method of claim 11, wherein the sensor includes a substrate on which the pH-sensitive composition is disposed.

15. The method of claim 11, wherein the feminine care absorbent article comprises an absorbent core positioned between a liquid-permeable layer and a liquid-impermeable layer.

16. The method of claim 15, wherein the antimicrobial composition is disposed on the liquid-permeable layer of the feminine care absorbent article.

17. The method of claim 15, wherein the sensor is disposed on the liquid-impermeable layer.

18. The method of claim 11, wherein the second color is indicative of the presence of perspiration within the absorbent article.

19. The feminine care absorbent article of claim 1, wherein the organic hydrophilic binder comprises carrageenan, pectin, gelatin, methylcellulose, cationized starch, carboxymethylcellulose, carboxymethylated starch, nitrocellulose, polyvinyl alcohol, polyvinylpyrrolidone, polyacrylic acid, polyacrylamide, a maleic acid copolymer, cellulose acetate, cellulose butyrate, or combinations thereof.

20. The feminine care absorbent article of claim 9, wherein the organic hydrophilic binder comprises carrageenan, pectin, gelatin, methylcellulose, cationized starch, carboxymethylcellulose, carboxymethylated starch, nitrocellulose, polyvinyl alcohol, polyvinylpyrrolidone, polyacrylic acid, polyacrylamide, a maleic acid copolymer, cellulose acetate, cellulose butyrate, or combinations thereof.

21. The method of claim 11, wherein the organic binder comprises carrageenan, pectin, gelatin, methylcellulose, cationized starch, carboxymethylcellulose, carboxymethylated starch, nitrocellulose, polyvinyl alcohol, polyvinylpyrrolidone, polyacrylic acid, polyacrylamide, a maleic acid copolymer, cellulose acetate, cellulose butyrate, or combinations thereof.

\* \* \* \* \*